US011678942B2

(12) United States Patent
Shao et al.

(10) Patent No.: US 11,678,942 B2
(45) Date of Patent: Jun. 20, 2023

(54) DEVICE, METHOD AND SYSTEM FOR REGISTRATION

(71) Applicant: Suzhou MicroPort Orthobot Co., Ltd., Jiangsu (CN)

(72) Inventors: Hui Shao, Jiangsu (CN); Bin Song, Jiangsu (CN); Chao He, Jiangsu (CN); Pengfei Liu, Jiangsu (CN)

(73) Assignee: SUZHOU MICROPORT ORTHOBOT CO., LTD., Jiangsu (CN)

( * ) Notice: Subject to any disclaimer, the term of this patent is extended or adjusted under 35 U.S.C. 154(b) by 360 days.

(21) Appl. No.: 16/856,372

(22) Filed: Apr. 23, 2020

(65) Prior Publication Data

US 2021/0186629 A1 Jun. 24, 2021

(30) Foreign Application Priority Data

Dec. 18, 2019 (CN) .......................... 201911312439.7

(51) Int. Cl.
*A61B 34/20* (2016.01)
*A61B 34/30* (2016.01)
(Continued)

(52) U.S. Cl.
CPC ............ *A61B 34/30* (2016.02); *A61B 5/0064* (2013.01); *A61B 34/20* (2016.02); *B25J 9/1628* (2013.01);
(Continued)

(58) Field of Classification Search
CPC .............................................. A61B 2090/3916
See application file for complete search history.

(56) References Cited

U.S. PATENT DOCUMENTS

2005/0198849 A1 9/2005 Goeggelmann et al.
2007/0123894 A1* 5/2007 Claypool ............... A61B 17/92
606/85
(Continued)

FOREIGN PATENT DOCUMENTS

CN 102258399 A 11/2011
CN 202614803 U 12/2012
(Continued)

*Primary Examiner* — Bill Thomson
*Assistant Examiner* — Aminah Asghar
(74) *Attorney, Agent, or Firm* — Muncy, Geissler, Olds & Lowe, P.C.

(57) ABSTRACT

The application provides a device, method and system for registration. The registration device includes a fixing member; a frame connected to the fixing member, at least one trackable element mounted on the frame; and a collection device connected to the fixing member, wherein the collection device is configured to simultaneously collect multiple point data from an object to be registered. The registration method includes obtaining simultaneously, by a registration device, a point cloud data from a surface of a cartilage of an object to be registered; and performing surface fitting based on the point cloud data to obtain a fitted surface of the cartilage of the object to be registered. The registration system includes the registration device; a first point cloud data acquisition module, configured to receive the point cloud data from the collection device; and a surface fitting module, configured for surface fitting with the point cloud data.

10 Claims, 14 Drawing Sheets

(51) Int. Cl.
  *B25J 9/16* (2006.01)
  *A61B 5/00* (2006.01)
  *A61B 90/00* (2016.01)
(52) U.S. Cl.
  CPC ............... *A61B 2034/2068* (2016.02); *A61B 2090/3916* (2016.02); *G05B 2219/40415* (2013.01); *G05B 2219/45117* (2013.01)

(56) References Cited

U.S. PATENT DOCUMENTS

2008/0208081 A1* 8/2008 Murphy ................. A61B 90/36
  600/595
2015/0005622 A1 1/2015 Zhao et al.
2020/0337782 A1* 10/2020 Glassman .......... A61B 17/1757

FOREIGN PATENT DOCUMENTS

| CN | 107124867 A | 9/2017 |
| CN | 108175501 A | 6/2018 |
| CN | 207456642 U | 6/2018 |
| CN | 108469934 A | 8/2018 |
| CN | 109567942 A | 4/2019 |
| CN | 208974098 U | 6/2019 |
| CN | 110169820 A | 8/2019 |
| CN | 110443839 A | 11/2019 |
| CN | 110960321 A | 4/2020 |

* cited by examiner

DEVICE, METHOD AND SYSTEM FOR REGISTRATION

CROSS-REFERENCE TO RELATED APPLICATION

This application claims the priority of Chinese patent application number 201911312439.7, filed on Dec. 18, 2019, the entire contents of which are incorporated herein by reference.

TECHNICAL FIELD

The present application relates to the technical field of medical instruments and, more specifically, to a device, method and system for registration.

BACKGROUND

Surgical navigation systems are widely used in surgical procedures, especially orthopedic surgery. For example, the MAKO orthopedic surgical navigation system and the Robodoc orthopedic surgical navigation system are both equipped with robotic arms and infrared optical navigation equipment. According to the preoperative planning and the registration technology during the operation, a doctor may rely on the robot-assisted technology to perform and complete a surgery. The bone registration technology is important for obtaining a coordinate conversion relationship between the virtual bone model of the navigation system and the actual bone. However, the existing registration tools and methods have the following problems:

(1) The procedure is cumbersome and thus the surgical time is extra added. The existing bone registration method includes: using a probe with a target trackball to perform a single-point collection of the bone. However, such single-point collection is low in speed, and limited in the number of samples that can be collected. In addition, the misoperation which may occur in manual collection of points may easily cause a failure of registration and thus increase the overall operation time.

(2) Soft tissue covers the bone surface, and thus it requires a probe with a pointed end to pierce the soft tissue so that the bone registration can be done. The intensity and depth of the puncture to the soft tissue are difficult to control manually. Therefore, the collection of points is not accurate enough, and a great error may occur in the collection of points, which causes a greater error in registration.

(3) The information of the soft tissue on the bone surface, which includes useful information for bone ligament balance analysis, cannot be obtained by the existing bone registration method.

SUMMARY OF THE INVENTION

The purpose of the present application is to provide a registration device, registration method and registration system, which can solve one or more of the problems of cumbersome registration procedures, great bone registration errors, and long registration time in the prior art.

In order to solve the above technical problem, in one aspect, the present application provides a registration device, comprising:

a fixing member;

a frame connected to the fixing member, at least one trackable element mounted on the frame; and a collection device connected to the fixing member, wherein the collection device is configured to simultaneously collect multiple point data from an object to be registered.

Optionally, the collection device comprises at least one of:

a first collection device configured to collect a first group of point data from the object to be registered; and a second collection device configured to collect a second group of point data from the object to be registered;

wherein the first collection device comprises a plurality of pointed probes, and the second collection device comprises a plurality of blunt probes.

Optionally, the plurality of pointed probes are arranged in an array; and/or the plurality of blunt probes are arranged in an array.

Optionally, each of the pointed probes and/or the blunt probes comprises:

a hollow housing; and a probe pin which is at least partially disposed in the housing and is axially moveable;

wherein the housing is connected to the fixing member, and two ends of the probe pin protrude out of the housing.

Optionally, a retractable member is provided in the housing, a rear end of the retractable member is connected to the housing, and a front end of the retractable member is connected to the probe pin.

Optionally, the retractable member is a spring, the retractable member is sleeved over the probe pin, an end of the housing which is close to the fixing member is provided with a stop collar, the probe pin has a stepped surface, the rear end of the retractable member is connected to the stop collar, and the front end of the retractable member is connected to the stepped surface.

Optionally, at least one of the pointed probes is at least partially located within one of the blunt probes and is axially movable.

Optionally, each of the blunt probes comprises:

a hollow housing connected to the fixing member; and a blunt probe pin that is at least partially disposed in the housing and is axially moveable;

wherein each of the pointed probes comprises a pointed probe pin, and at least a part of the pointed probe is located in the blunt probe and is moveable axially back and forth.

Optionally, a first retractable member is provided in the housing, and a second retractable member is provided inside an end of the blunt probe pin that is far away from the fixing member, wherein a rear end of the first retractable member is connected to the housing, and a front end of the first retractable member is connected to the blunt probe pin; and wherein a rear end of the second retractable member is connected to the blunt probe pin, and a front end of the second retractable member is connected to the pointed probe pin.

Optionally, the first retractable member and the second retractable member are both springs, the first retractable member is sleeved over the blunt probe pin, an end of the housing which is close to the fixing member is provided with a stop collar, the blunt probe pin has a stepped surface, the rear end of the first retractable member is connected to the stop collar, and the front end of the first retractable member is connected to the stepped surface; a stopper is provided inside an end of the blunt probe pin that is far away from the fixing member, the pointed probe pin comprises a horizontal portion and a vertical portion connected to the horizontal portion, the vertical portion has a pointed end that is far away from the fixing member, the rear end of the second retractable member is connected to the stopper, and the front end of the second retractable member is connected to the horizontal portion.

Optionally, the second collection device comprises a deformation member configured to deform correspondingly to a surface to be registered after being abutted against the surface be registered.

Optionally, a plurality of through holes are defined in the deformation member, and each of the through holes receives a pointed probe which is axially movable.

Optionally, the pointed probe comprises a housing and a probe pin disposed in the housing, the probe pin is moveable back and forth along an axial direction of the housing, a rear end of the probe pin protrudes out of a rear end of the housing, a front end of the probe pin protrudes out of a front end of the housing and is received in a corresponding one of the through holes.

Optionally, a retractable member is provided in the housing, a rear end of the retractable member is connected to the housing, and a front end of the retractable member is connected to the probe pin.

Optionally, the retractable member is a spring, the retractable member is sleeved over the probe pin, and an end of the housing which is close to the fixing member is provided with a stop collar, the probe pin has a stepped surface, the rear end of the retractable member is connected to the stop collar, and the front end of the retractable member is connected to the stepped surface.

Optionally, a sensor configured to measure a displacement and/or a deformation of the collection device is mounted on the collection device.

In another aspect, the present application provides a registration method, comprising:

obtaining simultaneously, by a registration device, a point cloud data from a surface of a cartilage of an object to be registered; and performing surface fitting based on the point cloud data to obtain a fitted surface of the cartilage of the object to be registered.

Optionally, the registration method comprises:

obtaining a first point cloud data from a surface of a bone of the object to be registered;

calculating a distance from each point of the first point cloud data to the fitted surface of the cartilage;

removing, according to a first preset threshold and a second preset threshold, points with a distance greater than the first preset threshold or less than the second preset threshold from the first point cloud data of the surface of the bone to obtain a second point cloud data of the surface of the bone, wherein the first preset threshold is greater than the second preset threshold; and performing a spatial registration with the second point cloud data and a three-dimensional model, which is obtained in advance, of the bone of the object to be registered to obtain a mapping relationship between a model space and a real space.

In still another aspect, the present application provides a registration system, comprising:

a registration device, comprising:

a fixing member;

a frame connected to the fixing member, at least one trackable element mounted on the frame; and a collection device connected to the fixing member, wherein the collection device is configured to simultaneously collect a point cloud data from a surface of a cartilage of an object to be registered;

a first point cloud data acquisition module, configured to receive the point cloud data from the collection device; and a surface fitting module, configured for surface fitting with the point cloud data.

Optionally, the registration system further comprises:

a second point cloud data acquisition module, configured to receive a first point cloud data from a surface of a bone of the object to be registered, the first point cloud data collected by the collection device;

a distance calculation module, configured to calculate a distance from each point of the first point cloud data to the fitted surface of the cartilage;

a selecting module, configured to remove, according to a first preset threshold and a second preset threshold, points with a distance greater than the first preset threshold or less than the second preset threshold from the first point cloud data from the surface of the bone to obtain a second point cloud data of the surface of the bone, wherein the first preset threshold is greater than the second preset threshold; and a registration module, configured to perform a spatial registration with the second point cloud data and a three-dimensional model, which is obtained in advance, of the bone of the object to be registered to obtain a mapping relationship between a model space and a real space.

Compared with the prior art, the registration device, registration method and registration system according to the present application have the following advantages:

(1) The registration device provided by the present application includes a fixing member and a collection device connected to the fixing member, and the collecting device is configured to simultaneously collect multiple point data from an object to be registered. As a result, it is possible, by using the registration device according to the present application, to selectively or simultaneously collect data of multiple points from the cartilage surface and/or the bone surface of the object to be registered, which greatly reduces the registration time of the object to be registered. Moreover, it is also possible, by using the registration device according to the present application, to selectively or simultaneously collect point cloud data of from the cartilage surface and/or the bone surface of the object to be registered, there is no need to manually select the points to be collected, which allows a simpler operation and thus less registration error.

(2) The registration method according to the present application includes: obtaining simultaneously, by a registration device, multiple point data from a surface of a cartilage of an object to be registered; and performing surface fitting based on the multiple point data to obtain a fitted surface of the cartilage of the object to be registered. As a result, the information of the soft tissue covering the bone surface will be obtained so that useful information is available in bone ligament balance analysis.

Figure 1:
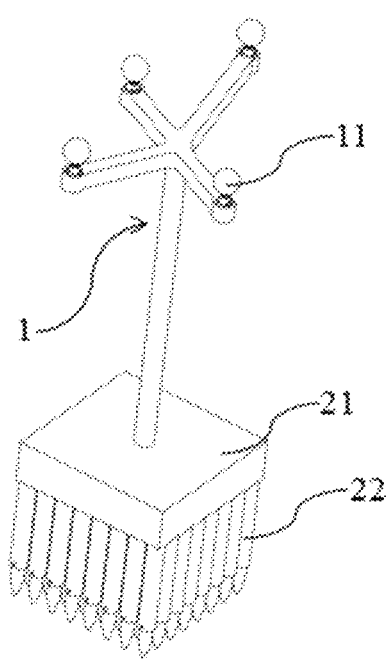
FIG. 1 is a schematic diagram showing a structure of a registration device provided with blunt probes according to a first embodiment of the present application.

The reference numerals are listed as follows:

navigation reference frame-1; target ball-11; fixing member-21; blunt probe-22; pointed probe-22'; sensor-3; deformation member-23; housing-221; probe pin-222, 222'; retractable member-223; stop collar-2211; stepped surface-2221; blunt probe pin-224; pointed probe pin-225; first retractable element-226; second retractable element-227; stopper-2241; horizontal portion-2251; vertical portion-2252; through hole-231; first connecting portion-2242; second connecting portion-2243; clip block-2244; mounting hole-2245; bone to be registered-4; cartilage surface-41; bone surface-42; threaded hole-211; point cloud data acquisition module-201; surface fitting module-202; distance calculation module-203; selecting module-204; registration module-205; processor-301; communication interface-302; memory-303; communication bus-304.

DETAILED DESCRIPTION

The registration device, registration method, registration system, electronic apparatus, and storage medium provided by the present application will be further described in detail below with reference to FIGS. 1 to 20. The advantages and features of the present application will become clearer from the following description. It should be noted that the drawings are in a very simplified form and all use inaccurate proportions, which are only used to facilitate the understanding of the description of the embodiments of the present application. In order to make the objects, features, and advantages of the present application more comprehensible, please refer to the accompanying drawings. It should be noted that the structures, proportions, sizes, etc. shown in the drawings in this specification are only used to illustrate the content disclosed in the specification for those familiar with this technology to understand and read, and are not intended to limit the implementation of the application. Any structural modification, change in proportional relationship, or adjustment of size should still fall within the scope of the present application without affecting the effects and goals that can be achieved by the present application.

It should be noted that, in the present application, relational terms such as first and second are used only to distinguish one entity or operation from another entity or operation, and do not necessarily require or imply that there is any such actual relationship or order among these entities or operations. Moreover, the terms "including", "comprising", or any other variation thereof are intended to encompass non-exclusive inclusion, such that a process, method, article, or device that includes a series of elements includes not only those elements but also those are not explicitly listed or other elements inherent to such a process, method, object, or device. Without more restrictions, the elements defined by the sentence "including a . . . " do not exclude the existence of other identical elements in the process, method, object, or device.

In the description of the present application, it should be understood that the terms "center", "longitudinal", "transverse", "length", "width", "thickness", "upper", "down", "front", "rear", "left", "right", "vertical", "horizontal", "top", "bottom", "inside", "outside", "axial", "radial", "circumferential" for indicating orientation or positional relationship is based on the orientation or positional relationship shown in the drawings, and is only for the convenience of describing the application and simplifying description. It does not indicate or imply that the referred device or element must have a specific orientation, or must be operated in such specific orientation, and thus they cannot be understood as a limitation to the present application. In the description of the present application, unless otherwise stated, "a plurality" means two or more.

In the description of the present application, the terms "installed", "connected", "coupled", and "fixed" should be understood in a broad sense unless specified and limited otherwise. For example, they may be fixed connections or removable connections or integrated; it can be mechanical or electrical connection; it can be directly connected, or it can be indirectly connected through an intermediate medium, it can be the internal connection of the two elements or the interaction between the two elements. For those of ordinary skill in the art, the specific meanings of the above terms in the present application can be understood.

In the present application, unless specifically stated and defined otherwise, the first feature being "above" or "below" the second feature may include the cases that the first and second features are in contact with each other directly, and may also include that the first and second features are in contact with each other indirectly, but through another feature contact between them. Moreover, the first feature being "above", "over", and "on" the second feature, including the cases that the first feature is right above and obliquely above the second feature, or merely indicates that the first feature is higher in level than the second feature. The first feature being "below", "under", and "beneath" the second feature, including the cases that the first feature is right below and obliquely below the second feature, or merely indicates that the first feature is lower in horizontal level than the second feature.

The core idea of the present application is to provide a registration device, a registration method, a registration system, an electronic device, and a storage medium to solve one or more of the problems of cumbersome registration procedures, great bone registration errors, and long registration time in the prior art.

To achieve the above idea, the present application provides a registration device. The registration device is a registration target including a fixing member and a collection device connected to the fixing member, and the collecting device is configured to collect multiple point data on from an object to be registered simultaneously. As a result, it is possible, by using the registration device according to the present application, to selectively or simultaneously collect data of multiple points from the cartilage surface and/or the bone surface of the object to be registered, which greatly reduces the registration time of the object to be registered. Moreover, it is also possible, by using the registration device according to the present application, to selectively or simultaneously collect point cloud data of from the cartilage surface and/or the bone surface of the object to be registered, there is no need to manually select the points to be collected, which allows a simpler operation and thus less registration error. It shall be noted that the object to be registered can be an object other than a bone, which is not limited here.

Preferably, the collection device includes at least one of a first collection device configured to collect a first group of point data from an object to be registered and a second collection device configured to collect a second group of point data from an object to be registered. When a bone is selected as the object to be registered, the first group of point data refers to a group of point data from a surface of the bone to be registered, and the second group of point data refers to a group of point data from a surface of a cartilage covering the bone to be registered.

In some embodiments, the first collection device includes a plurality of pointed probes, and the second collection device includes a plurality of blunt probes. Thus, the pointed probes are configured to collect the point data from the surface of the bone to be registered, and the blunt probes are configured to collect the point data from the surface of the cartilage covering the bone to be registered.

In some embodiments, the plurality of pointed probes are arranged in an array; and/or the plurality of blunt probes are arranged in an array. As a result, the collection device can cover a larger area of the bone to be registered, so that more point data can be collected simultaneously.

In some embodiments, the second collection device includes a deformation member configured to deform correspondingly to a surface to be registered after being abutted against the surface be registered. As a result, the deformation member will deform correspondingly to a surface to be registered after being abutted against the surface of the cartilage covering the bone to be registered. Therefore, multiple point data can be collected from the surface of the cartilage.

In some embodiments, a sensor configured to measure a displacement and/or a deformation of the collection device is mounted on the collection device. As a result, a displacement and/or a deformation of the pointed probe and the blunt probe of the collection device can be measured accurately. Therefore, multiple point data can be collected from an object to be registered in a more accurate way.

In some embodiments, the registration target further includes a navigation reference frame connected to the fixing member, and the navigation reference frame is provided with at least three target balls. As a result, the registration can be performed in a more convenient way.

Preferably, the navigation reference frame is connected to the fixing member detachably. As a result, a fixing member connected with a certain collection device can be selected according to actual needs to be connected to the navigation reference frame, so that a collection of point data from a corresponding object or different objects to be registered can be done, which can effectively reduce costs.

Figure 12:
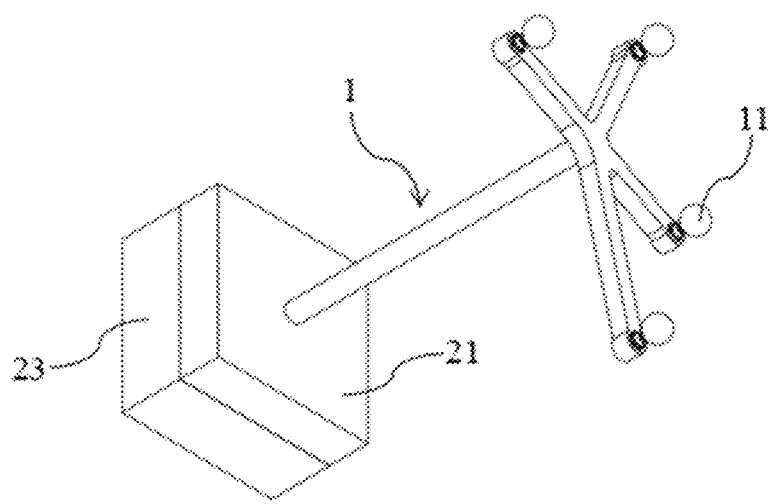
FIG. 12 is a schematic diagram showing a structure of a registration device according to a third embodiment of the present application.
Figure 13:
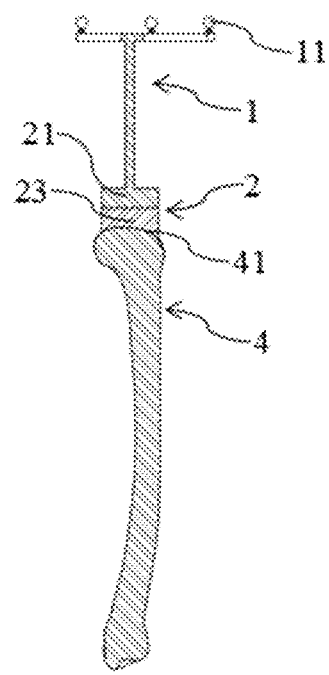
FIG. 13 is a schematic diagram showing a deformation of the registration device shown in FIG. 12 when acting onto a bone surface.
Figure 14:
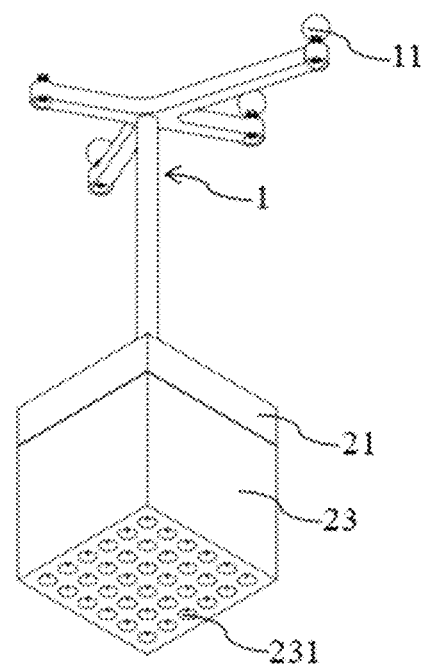
FIG. 14 is a schematic diagram showing a structure of a registration device according to a fourth embodiment of the present application.
Figure 15:
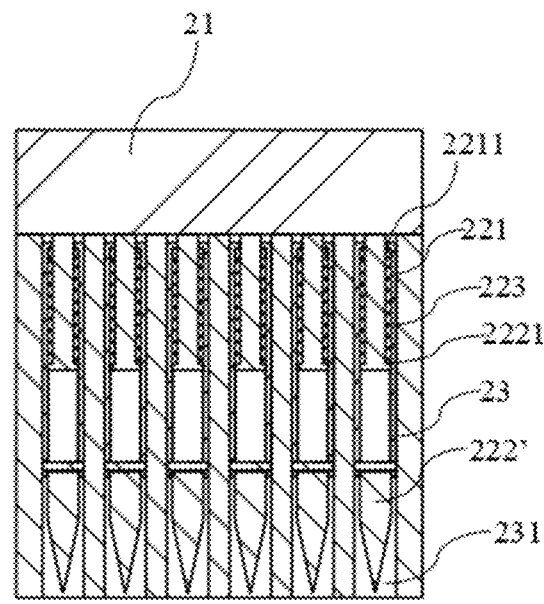
FIG. 15 is a schematic diagram showing a structure of a collection device of a registration device shown in FIG. 14.
Figure 16:
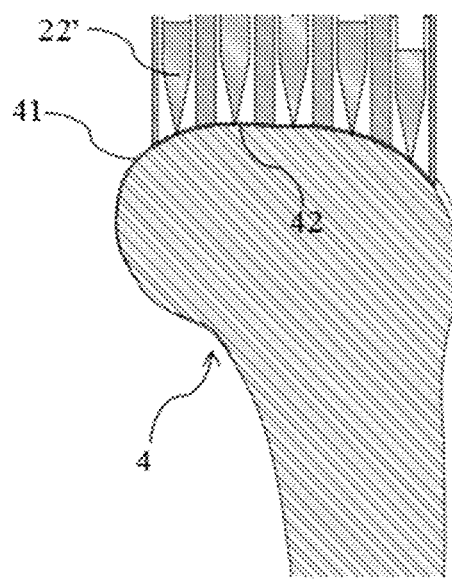
FIG. 16 is a schematic diagram showing a deformation of the registration device shown in FIG. 14 when acting onto a bone surface.

Please refer to FIGS. 1 to 14. FIGS. 1 to 7 schematically illustrate the overall structure of a registration target according to the first embodiment of the present application. FIGS. 8 to 11 schematically illustrate the overall structure of a registration target according to the second embodiment of the present application. FIGS. 12 to 13 schematically illustrate the overall structure of a registration target according to the third embodiment of the present application. FIGS. 14 to 16 schematically illustrate the overall structure of a registration target according to the fourth embodiment of the present application. As shown in FIGS. 1, 4, 8, 12 and 14, the registration target includes a navigation reference frame 1, a fixing member 21, and a collection device connected to the fixing member 21. The navigation reference frame 1 is provided with four target balls 11. It should be noted that the number of the target balls 11 is at least three and can be determined according to specific circumstances. For example, in other embodiments, it can be determined as three, five or more, which is not limited thereto.

As shown in FIGS. 1 to 11, the collection device includes a plurality of blunt probes 22/pointed probes 22' arranged in an array. The rear end of the fixing member 21 is connected to the navigation reference frame 1. The front end of the fixing member 21 is connected to the plurality of blunt probes 22/pointed probes 22' arranged in an array. The blunt probes 22/pointed probes 22' can be deformed towards or backwards the fixing member 21. The blunt probes 22/pointed probe 22' is configured to come into contact with an object to be registered, for example, the bone 4 to be registered. Each of the blunt probes 22/pointed probe 22' is provided with a sensor 3 configured to measuring the displacement of the blunt probe 22/pointed probe 22'. Since the collection device includes a plurality of blunt probes 22/pointed probes 22' arranged in an array, and each of the blunt probes 22/pointed probes 22' is installed with a sensor 3 for measuring the displacement thereof, the registration target provided by the present application can simultaneously collect a group of point data/point cloud data from the surface 41 of the cartilage covering the bone 4 to be registered and/or surface 42 of the bone 4 to be registered, thus greatly reducing the registration time consumed in registration of the bone 4 to be registered. The group of point data or point cloud data according to this application refers to a set of multiple point data simultaneously collected from the surface of the cartilage covering the bone 4 to be registered and/or surface of the bone 4 to be registered by the registration target. Further, since the registration target provided by the present application can simultaneously collect point cloud data from the surface 41 of the cartilage covering the bone 4 to be registered and/or surface 42 of the bone 4 to be registered, there is no need to manually select sampling points multiple times, which is more convenient for operation, effectively avoids human error, and thus reduces registration errors. In addition, since a sensor 3 is mounted on each of the blunt probes 22/pointed probes 22', the displacements of the blunt probes 22/pointed probes 22' can be accurately measured by the sensors 3. In addition, since the blunt probes 22/pointed probes 22' can be deformed to be close to or far away from the fixing member 21, the registration target provided by the present application suitable for the measurement of surface data of bones having various shapes. According to the present application, the front end refers to an end close to the object to be registered, and the rear end refers to an end far away from the object to be registered.

It should be noted that, in the present application, the sensor 3 is a distance sensor, a position sensor, or a pressure sensor. When a pressure sensor is used, a pressure value can be obtained through the pressure sensor, and then the pressure value will be converted into the displacement amount of a blunt probe 22/pointed probe 22'; when a distance sensor is used, the distance sensor is an LVDT displacement sensor or a potential sensor. The sensor 3 can be a sensor capable of measuring a displacement amount other than the above-mentioned sensor, and the present application is not limited thereto.

Figure 2:
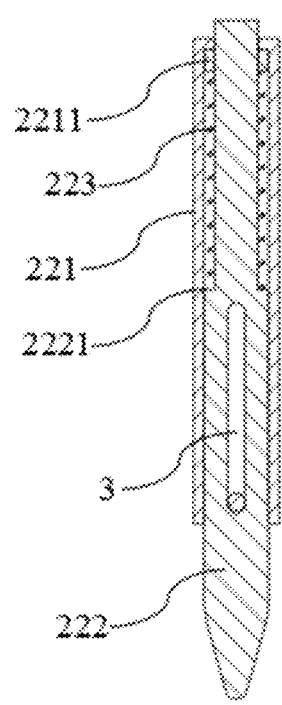
FIG. 2 is a schematic diagram showing a structure of a blunt probe of the registration device shown in FIG. 1.
Figure 3:
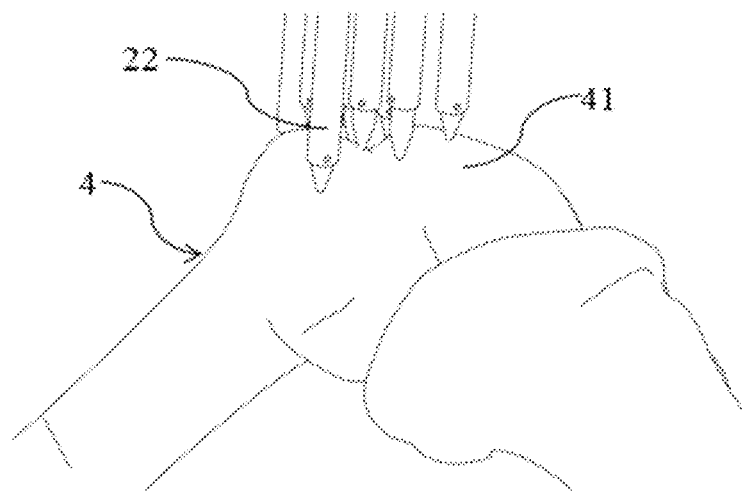
FIG. 3 is a schematic diagram showing a deformation of the registration device shown in FIG. 1 when acting onto a bone surface.
Figure 4:
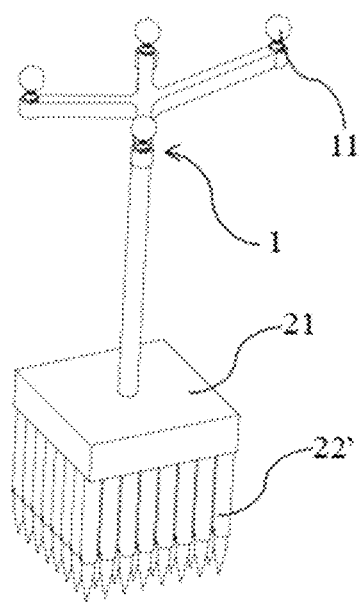
FIG. 4 is a schematic diagram showing a structure of a registration device provided with pointed probes according to a first embodiment of the present application.

Preferably, as shown in FIGS. 1 to 7, in a first embodiment, the collection device includes a first collection device and a second collection device. As shown in FIGS. 1 to 3, the second collection device includes a plurality of blunt probes 22 arranged in an array. Each of the blunt probes 22 includes a hollow housing 221 and a probe pin 222 at least partially disposed in the housing 221. The housing 221 is connected to the fixing member 21, the rear end of the probe pin 222 protrudes out of the rear end of the housing 221, and the fixing member 21 is defined with holes (not shown) matched with the rear ends of the probes pin 222. The rear end of each probe pin 222 can extend into a corresponding one of the holes of the fixing member 21, so that the probe pin 222 is moveable back and forth in the axial direction of the hole; the front end of the probe pin 222 extends out of the front end of the housing 221 and is configured to contact the surface 41 of the cartilage covering the bone 4 to be registered; the probe pin 222 is moveable back and forth along the axial direction of the housing 221, and the probe pin 222 has a blunt end which is far away from the fixing member 21, and the sensor 3 is mounted on the probe pin 222 and is configured to measure the displacement of the probe pin 222. Since the end of the probe pin 222 far from the fixing member 21 is a blunt end, the registration target provided in this embodiment is capable of collecting point cloud data of the surface 41 of the cartilage covering the bone 4 to be registered.

Preferably, as shown in FIGS. 4 to 7, the first collection device includes a plurality of pointed probes 22' arranged in an array. Each of the pointed probe 22' includes a hollow housing 221 and a probe pin 222' at least partially disposed in the housing 221. The pointed probe 22' has a structure almost same as that of the blunt probe 22 described above except that the probe 222' of the pointed probe 22' has a pointed end which is far away from the fixing member 21. The sensor 3 is mounted on the probe pin 222' and is configured to measure the displacement of the probe 222'. Since the end of the probe 222' which is far away from the fixing member 21 is a pointed end, the pointed end can easily pierce the soft tissue of the bone 4 to be registered and then contact the surface of the bone 4 to be registered. Therefore, the registration target provided in this embodiment is capable of collecting point cloud data of the surface 42 of the bone 4 to be registered.

In practice, the point cloud data of the surface 41 of the cartilage covering the bone 4 to be registered and the point cloud data of the surface 42 of the bone 4 to be registered can both be collected through the registration target as described in the first embodiment of the present application, thereby registration for the bone 4 to be registered can be completed.

Figure 7:
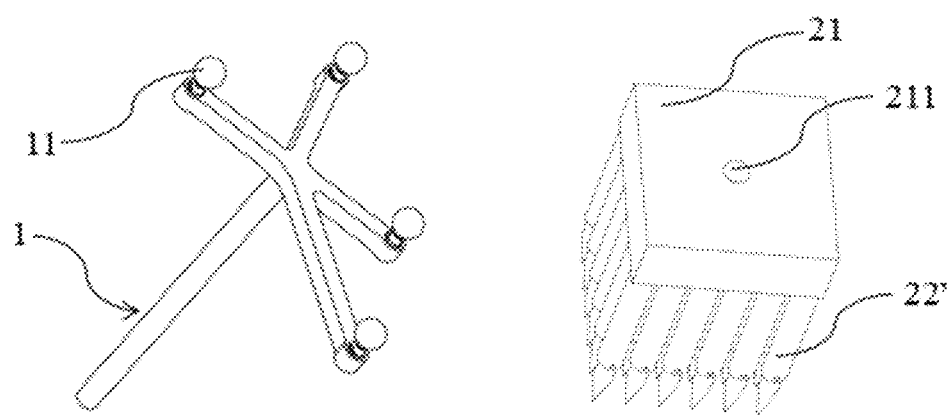
FIG. 7 is an exploded view of the registration device shown in FIG. 4.
Figure 8:
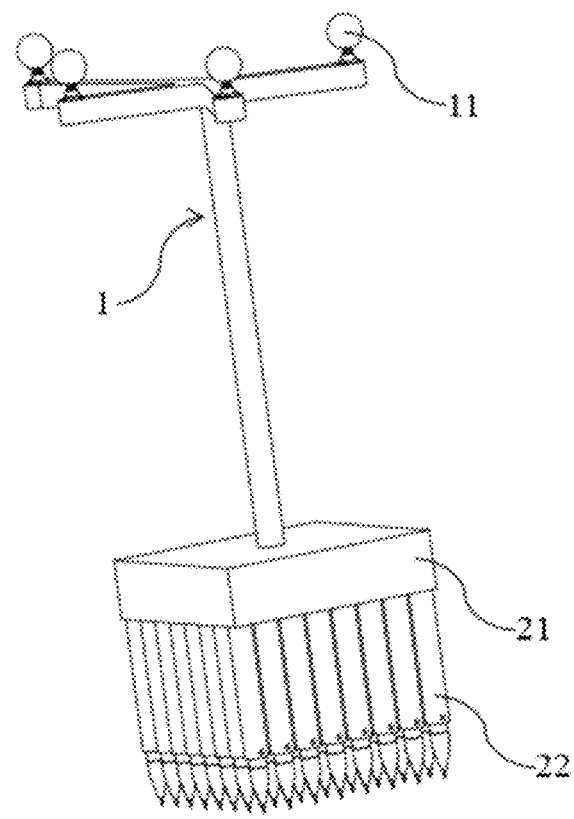
FIG. 8 is a schematic diagram showing of a structure of a registration device according to a second embodiment of the present application.

In order to further save costs, as shown in FIG. 7, the navigation reference frame 1 and the fixing member 21 are detachably connected. As a result, when the point cloud data of the cartilage surface 41 needs to be collected, the fixing member 21 connected to the second collection device which has a plurality of blunt probes 22 can be selected to connect to the navigation reference frame 1, so that the point cloud data of the surface 41 of the cartilage covering bone 4 to be registered can be measured through a plurality of blunt probes 22 arranged in an array. When the point cloud data of the bone surface 42 needs to be collected, the fixing member 21 connected to the first collection device which has a plurality of pointed probes 22' can be selected to connect to the navigation reference frame 1, so that the point cloud data of the surface 42 of the bone 4 to be registered can be measured through a plurality of blunt probes 22' arranged in an array.

In some embodiments, the navigation reference frame 1 has external threads (not shown in the figure) at an end thereof close to the fixing member 21, and the fixing member 21 has a screw hole 211 at an end thereof close to the navigation reference frame 1, and the screw hole 211 matches with the external threads. As a result, the navigation reference frame 1 can be connected to the fixing member 2 detachably. It should be noted that, in some other embodiments, the navigation reference frame 1 can be connected to the fixing member 2 in other ways known in prior art, which is not limited in the present application.

Figure 5:
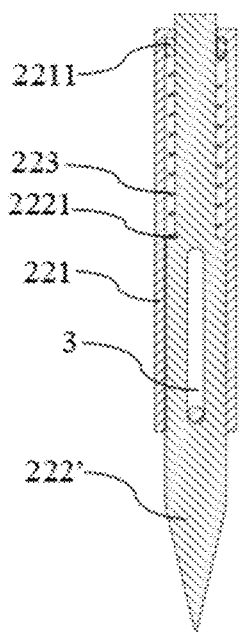
FIG. 5 is a schematic diagram showing a structure of a pointed probe of the registration device shown in FIG. 4.
Figure 6:
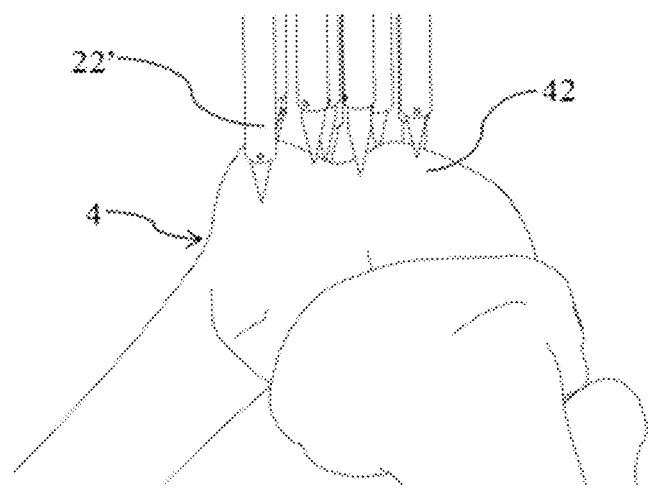
FIG. 6 is a schematic diagram showing a deformation of the registration device shown in FIG. 4 when acting onto a bone surface.

Preferably, as shown in FIGS. 2 and 5, a retractable member 223 is provided in the casing 221, and the retractable member 223 is located between the casing 221 and the probe pin 222. Therefore, by providing the retractable element 223 in the housing 221, not only the probe pin 222 can easily move back and forth, but also the overall structure of the registration target provided by the present application can be simplified.

Preferably, as shown in FIGS. 2 and 5, the retractable member 223 is a spring, the retractable member 223 is sleeved over the probe pin 222/probe pin 222'. An end of the housing 221 which is close to the fixing member 21 is provided with a stop collar 2211, the probe pin 222/probe pin 222' is extended through the stop collar 2211, the probe pin 222/probe pin 222' has a stepped surface 2221, and the retractable member 223 is located in a space defined by the stop collar 2211, the stepped surface 2221, the housing 221, and the probe pin 222/probe pin 222', at least one end of the retractable element 223 is connected to or abutted against the stop collar 2211 or the stepped surface 2221. Therefore, through using a spring as the retractable element 223, and the retractable element 223 is sleeved over the probe pin 222/probe pin 222', a space-saving structure can be achieved and thereby further simplifying the overall structure of the registration target provided by the present application. In addition, by providing a stop collar 2211 in the housing 221 and a stepped surface 2221 on the probe pin 222/probe pin 222', the retractable member 223 can be provided between the stop collar 2211 and the stepped surface 2221, thereby facilitating the installation of the retractable element 223 and effective control of the movement of the probe pin 222/probe pin 222'.

Preferably, as shown in FIGS. 8 to 11, in a second embodiment, the collection device includes both a first collection device and a second collection device. The first collection device includes a plurality of pointed probes 22' arranged in an array, and the second collection device includes a plurality of blunt probes 22 arranged in an array. The pointed probes 22' are arranged correspondingly to the blunt probes 22 one by one. Each of the blunt probes 22 includes a hollow housing 221 and a blunt probe pin 224 at least partially disposed in the housing 221. The housing 221 is connected to the fixing member 21. The rear end of the blunt probe 224 protrudes out of the rear end of the housing 221, and the fixing member 21 is provided with holes matching with the rear ends of the blunt probe pins 224. The rear ends of the blunt probe pins 224 can be inserted into the hole, so that the blunt probe pins 224 can move back and forth in the axial direction of the holes. The front end of the blunt probe pin 224 extends out of the front end of the housing 221 and is configured to contact the cartilage covering the bone 4 to be registered. The blunt probe pin 224 can move back and forth in the axial direction of the housing 221. Each of the pointed probes 22' includes a pointed probe pin 225. At least a part of the pointed probe 225 is located inside an end of the blunt probe pin 224 that is far away from the fixing member 21. The pointed probe 225 is moveable back and forth along the axial direction of the blunt probe pin 224. The front end of the blunt probe pin 224 is a blunt end, and the front end of the pointed probe 225 is a pointed end. The pointed probe pin 225 is configured to contact the bone 4 to be registered. A first sensor (not shown in the figures) configured to measure the displacement of the blunt probe pin 224 is mounted on the blunt probe 224, and a second sensor (not shown in the figures) configured to measure the displacement of the pointed probe pin 225 is measured on the pointed probe pin 225. In this embodiment, the collection device includes both blunt probe pins 224 and pointed probe pins 225, the collection of the point cloud data from the surface 41 of the cartilage covering the bone 4 to be registered is achieved through the blunt probe pins 224, and the collection of the point cloud data of the surface 42 of the bone 4 to be registered is achieved through the pointed probe pins 225, so that both the point cloud data of the cartilage surface 41 and the point cloud data of the bone surface 42 can be obtained simultaneously through the registration target provided in this embodiment. As a result, the operation is simpler, the time consumed in the operation is reduced and the efficiency of registration for the bone 4 to be registered is greatly improved.

Preferably, a first retractable element 226 is provided in the housing 221, and a second retractable element 227 is provided inside the end of the blunt probe pin 224 far away from the fixing member 21. The rear end of the first retractable element 226 is connected/contacted with the housing 221, and the front end of the first retractable member 226 is connected/contacted with the blunt probe pin 224. The rear end of the second retractable member 227 is connected/contacted with the blunt probe pin 224, and the front end of the second retractable element 227 is connected/contacted with the pointed probe pin 225. Since the first retractable element 226 is provided inside the housing 221 and the second retractable element 227 is provided inside the blunt probe pin 224, the reciprocation of the blunt probe pin 224 and the pointed probe pin 225 is achieved more easily while the overall structure of the registration target provided by the present application is further simplified.

Figure 9:
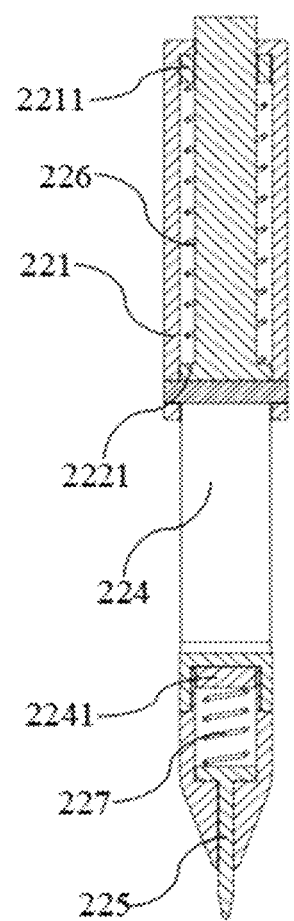
FIG. 9 is a schematic diagram showing a structure of a blunt probe and a pointed probe of the registration device shown in FIG. 8.
Figure 10:
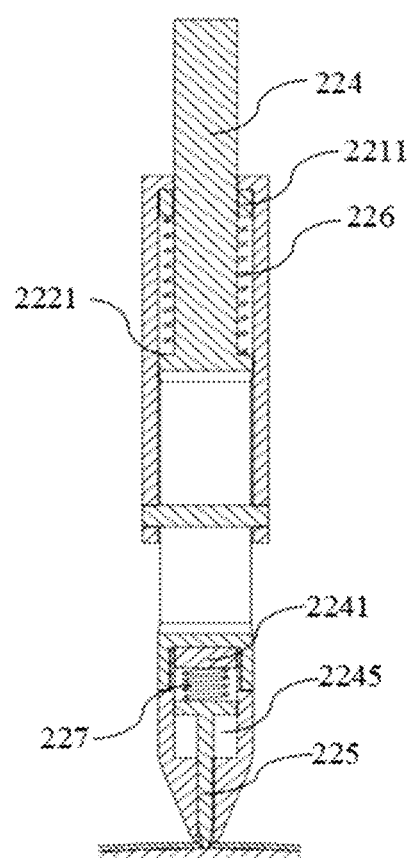
FIG. 10 is a schematic diagram showing deformations of the blunt probe and the pointed probe shown in FIG. 9 when they act onto the bone surface.
Figure 11:
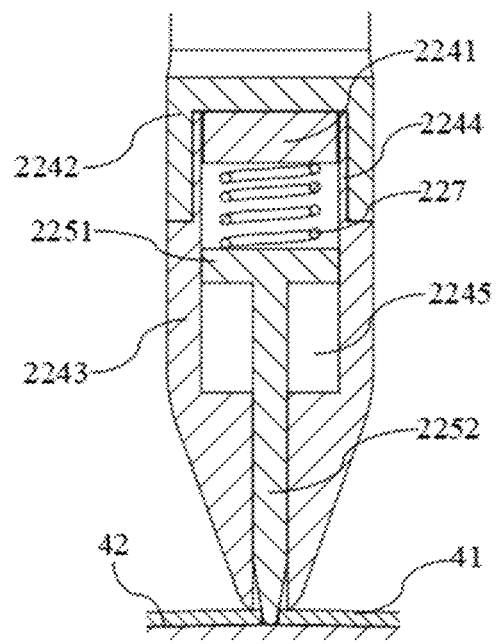
FIG. 11 is a partially enlarged view of the structure shown in FIG. 10.

In some embodiments, as shown in FIGS. 9 to 11, the first retractable element 226 and the second retractable element 227 are both springs, and the first retractable element 226 is sleeved over the blunt probe pin 224. A stop collar 2211 is provided at an end of the housing 221 close to the fixing member 21. A rear end of the blunt probe pin 224 extends through the stop collar 2211 and protrudes out of the housing 221. The blunt probe pin 224 is provided with a stepped surface 2221. The rear end of the first retractable member 226 is connected/contacted with the stop collar 2211, and the front end of the first retractable member 226 is connected/contacted with the stepped surface 2221. A stopper 2241 is provided inside the end of the blunt probe pin 224 far away from the fixing member 21. The pointed probe pin 225 includes a horizontal portion 2251 and a vertical portion 2252 connected to the horizontal portion 2251. An end of the vertical portion 2252 far away from the fixing member 21 is a pointed end. A rear end of the second retractable member 227 is connected to the stopper 2241, and a front end of the second retractable member 227 is connected to the horizontal portion 2251. Since the first retractable element 226 and the second retractable element 227 are both springs, and the first retractable element 226 is sleeved over the blunt probe pin 224, space is saved, and the overall structure of the registration target provided by the present application is further simplified. In addition, since a stop collar 2211 is provided inside the housing 221 and a stepped surface 2221 is provided on the blunt probe pin 224, it is possible to arrange the first retractable member 226 between the stop collar 2211 and the stepped surfaces 2221, which facilitates the installation of the first retractable element 226. Since a stopper 2241 is arranged inside the blunt probe pin 224 and the pointed probe pin 225 is designed to include a T-shaped structure defined by a horizontal portion 2251 and a vertical portion 2252, it is possible to arrange the second retractable member 227 between the stopper 2241 and the horizontal portion 2251, which facilitates the installation of the second retractable member 227.

In some embodiments, in order to facilitate the installation of the second retractable member 227, as shown in FIGS. 9 to 11, an end of the blunt probe pin 224 far away from the fixing member 21 includes a first connection portion 2242 and a second connection portion 2243 which are detachably connected. The blunt probe pin is arranged at a front end of the second connection portion 2243. An end of the first connection portion 2242 close to the second connection portion 2243 is provided with a slot. One end of the second connection portion 2243 close to the first connection portion 2242 is provided with a clamping block 2244 that cooperates with the slot. The second connection portion 2243 has a mounting hole 2245 that is matched with the pointed probe pin 225. The mounting hole 2245 includes a chamber for receiving the second retractable element 227 and allowing the horizontal portion 2251 to slide axially inside thereof, and a guide passage for receiving the pointed probe pin 225 and allowing the pointed probe pin 225 to slide axially. The stopper 2241 is disposed inside an end of the mounting hole 2245 close to the first connection portion 2242.

As shown in FIGS. 9 to 11, when the registration target provided in this embodiment is collecting data from the bone 4 to be registered, the pointed probe pin 225 is first brought into contact with the surface 41 of the cartilage covering the bone 4 to be registered, and then the registration target is further pressed downwards so that the pointed probe pin 225 pierces cartilage tissue and therefore abuts against the surface 42 of the bone. At this time, the pointed probe pin 225 is forced to move axially toward the inside of the mounting hole 2245 and further compresses the two retractable element 227. Since the bone surface 42 is uneven, each pointed probe pin 225 of the probe array will have different degrees of axial displacement. The second sensor installed on each pointed probe pin 225 will measure the corresponding displacement of the pointed probe pin 225 to complete the acquisition of the point cloud data of the bone surface 42. When the registration target is further pressed towards the bone 4 to be registered, the pointed probe pin 225 is fully contracted into the blunt probe pin 224, and at this time, the blunt end of the blunt probe pin 224 of the probe array contacts the surface 41 of the cartilage covering the bone 4 to be registered. As the cartilage surface 41 is also uneven, each blunt probe pin 224 of the probe array will also have different degrees of axial displacement. The first sensor installed on each blunt probe pin 224 will measure the corresponding displacement of the blunt probe pin 224 to complete the collection of point cloud data of the cartilage surface 41.

Based on the substantially same principle of the second embodiment as shown in FIGS. 8 to 11, as can be understood by those skilled in the art, in some embodiments, the front end of the fixing member 21 is connected with a blunt probe 22 and a pointed probe 22', there is a distance between the front end of the blunt probe 22 and the front end of the pointed probe 22', which is shown as a distance between the blunt probe 224 and the pointed probe 225 as shown in FIG. 9. In a free state where a surface contact is not achieved, the front end of the blunt probe 22 is retracted inward/upward with respect to the front end of the pointed probe 22' by a certain distance so that the blunt probe 22 will abut against the cartilage surface 41 after the pointed probe 22' abuts against the bone surface 42 and retracts upward by a certain distance. Therefore, point data sets of different surfaces will be obtained.

The NDI optical tracking system is taken as an example to explain the positioning principle of the registration target provided by the present application. Assuming that the coordinate origin of the registration target (the center of one of the target balls 11) at a certain moment in the NDI coordinate system is $O=\{x, y, z\}$, The set of conversion relations between the registration target and the pointed probe array is $T=\{t\_i, i=1,2, \ldots n\}$, where the $t\_i$ represents the conversion relationship between the i-th pointed probe 22 and the registration target, the set of conversion relationships between the registration target and the blunt probe array is $U=\{u\_i, i=1, 2, n\}$, where the $u\_i$ represents the conversion relationship between the i-th blunt probe 22 and the registration target. Therefore, according to the coordinate origin of the registration target and the set of conversion relations between the registration target and the probe array, the set of coordinates for the pointed probe array at a certain time in the NDI coordinate system can be obtained as $Q=\{q\_i, i=1, 2, n\}$, the set of coordinates for the blunt probe array is $P=\{p\_i, i=1,2, n\}$, where $q\_i=O\cdot t\_i$ and $p\_i=O\cdot u\_i$, where $q\_i$ represents the coordinate of the i-th pointed probe 22 in the NDI coordinate system, $p\_i$ represents the coordinate of the i-th blunt probe 22 in the NDI coordinate system.

When the point cloud data of the surface 41 of the cartilage covering the bone 4 to be registered is collected by using a blunt probe array, each blunt probe 22 in the blunt probe array will have displacement to various degrees because the cartilage surface 41 is uneven. Assuming that the set of the displacement amount of the blunt probe array is $\Delta X=\{\Delta x\_i, i=1,2, \ldots n\}$, wherein $\Delta x\_i$ represents the displacement amount of the i-th blunt probe 22 during its measurement, at this time, the set of conversion relations between the blunt registration target and the blunt probe array is $U'=\{u\_i', i=1,2, \ldots n\}$, where $u\_i'=u\_i-\Delta x\_i$, the point cloud data of the surface 41 of the cartilage covering the bone 4 to be registered, which is obtained by the blunt probe array, is $P'=\{p\_i, i=1,2, \ldots n\}$, wherein $p\_i'=O\cdot u\_i'$.

Similarly, when the point cloud data of the surface 42 of the bone 4 to be registered is collected by using a pointed probe array, each of the pointed probes 22' in the pointed probe array will have displacement to various degrees because the bone surface 42 is uneven. Assuming that the set of the displacement of the pointed probe array is $\Delta Y=\{\Delta y\_1, 2, \ldots n\}$, where $\Delta y\_i$ represents the displacement of the i-th pointed probe 22' during its measurement, at this time, the set of conversion relations between the pointed registration target and the pointed probe array is $T'=\{t\_i', i=1,2, \ldots n\}$, where $t\_i'=t\_i-\Delta y\_i$, the point cloud data of the surface 42 of the bone 4 to be registered, which is obtained by the pointed probe array, is $Q'=\{q\_i', i=1,2, \ldots n\}$, where $q\_i=O\cdot t\_i'$.

Please refer to FIGS. 12 and 13, which schematically show structure diagrams of a registration target provided by a third embodiment of the present application. As shown in FIGS. 12 and 13, in this embodiment, the collection device includes a second collection device including a deformation member 23. The rear end of the fixing member 21 is connected to the navigation reference frame 1, and the front end of the fixing member 21 is connected to the deformation member 23. The deformation member 23 is made of a shape memory material. A plurality of sensors (not shown) arranged in an array are installed onto the deformation member 23, the sensors are used to measure the deformation amount of the corresponding portion of the deforming member 23, and the deforming member 23 is used to contact with the bone 4 to be registered. Since the deformed member 23 is made of a shape memory material, the deformed member 23 will be deformed accordingly based on the shape of the cartilage surface 41 in the case that a registration target employing the deformed member 23 as its collection device is used to collect point cloud data from the cartilage surface 41. The sensors which are arranged in an array and installed on the deforming member 23 is configured to measure the amount of deformation (displacement) of various portions of the deforming member 23. As a result, a collection of point cloud data of the cartilage surface 41 will be completed. In addition, since the deformation member 23 covers a large area of the cartilage surface 41, more data about the cartilage can be collected at one time, and the accuracy of modeling of the cartilage surface 41 can be effectively improved.

The following takes the NDI optical tracking system as an example to explain the registration principle of the registration target provided in this embodiment. The registration target provided in this embodiment has target balls 11, the position and attitude information of which is known in the optical tracking system NDI, and the relationship between the coordinate of the point cloud data of the cartilage surface 41 collected by the deformation member 23 and the coordinate of the NDI is also known. Therefore, through conversion of coordinate, the coordinate conversion relationship (mapping relationship) between the bone (existed in real space) and the virtual model (existed in modeled space) of the bone can be obtained, thereby completing the entire registration process.

In this embodiment, the navigation reference frame 1 and the fixing member 21 are detachably connected. Therefore, it is also possible to connect the first collection device having a pointed probe array as described above in the first embodiment to the navigation reference frame 1 through the fixing member 21 of the first collection device after the point cloud data of the surface 41 of the cartilage covering the bone 4 to be registered is collected by the second collection device having the deforming member 23, so as to measure the point cloud data of the surface 42 of the bone 4 to be registered through the pointed probe array.

Preferably, please refer to FIGS. 14 to 16, which schematically show structure diagrams of a registration target provided by a fourth embodiment of the present application. In this embodiment, the collection device includes a first collection device and a second collection device. The first collecting device includes a deformation member while the second collecting device includes a plurality of pointed probes arranged in an array. As shown in FIGS. 14 to 16, the deforming member 23 is defined with a plurality of through holes 231 arranged in an array, and each of the through holes 231 is provided therein with a pointed probe 22' which is capable of moving back and forth axially along a corresponding one of the through holes 231. The specific principle of the pointed probe 22' is same as that described in the second embodiment above, so it will not be described in detail here. The pointed end of the pointed probe 22' is used to contact with the bone 4 to be registered, and a sensor (not shown in the figure) for measuring displacement of the pointed probe 22' is mounted on the pointed probe 22', and sensors (not shown) arranged in an array for measuring the amount of deformation of the deformable member 23 can be installed on the deformable member 23 where the through hole 231 is not located. Since the deforming member 23 is provided therein with a plurality of pointed probes 22' having pointed ends in an array, the point cloud data of the cartilage surface 41 will be collected when the deformed member 23 is deformed through abutting against the cartilage surface 41, and the point cloud of the surface 42 of the bone 4 to be registered will be collected when the pointed probes 22' having pointed ends in the through holes 231 is abutted against the bone surface 42. As a result, both the point cloud data of the cartilage surface 41 and the point cloud data of the bone surface 42 will be obtained through the registration target provided by this embodiment, which results in a simpler operation, an effectively reduced time consuming in the registration, and a higher registration efficiency for the registration of the bone 4 to be registered.

Preferably, as shown in FIG. 15, the pointed probe 22' includes a housing 221 and a probe pin 222' provided in the housing 221, and the probe 222' is capable of moving back and forth axially along the housing 221. The rear end of the probe 222' protrudes out of the rear end of the housing 221 and is connected to the fixing member. In some embodiments, the fixing member 21 is provided with holes matching the rear ends of the probe pins 222', and the holes are capable of receiving the probe pins 222', which allows the probe pins 222' to move back and forth axially along the holes. The front end of the probe 222' extends out of the front end of the housing 221 and has a pointed end, and a displacement sensor (not shown in the figure) for measuring the displacement of the probe pin 222' is mounted on the probe pin 222'. Therefore, the overall structure of the registration target provided by the present application is further simplified, and the pointed probes 22' can be moved back and forth in a simpler way and operated more conveniently.

In some embodiments, a retractable member 223 is provided in the housing 221. A rear end of the retractable member 223 is connected to the housing 221, and a front end of the retractable member 223 is connected to the probe pin 222'. Since the retractable member 223 is arranged in the housing 221, not only the reciprocating movement of the probe 222' is realized more conveniently, but also the overall structure of the registration target provided by the present application is further simplified.

In some embodiments, the retractable member 223 is a spring, and the retractable member 223 is sleeved over the probe pin 222'. A stop collar 2211 is provided on an end of the housing 221 close to the fixing member 21, and the probe pin 222' extends through the stop collar 2211. The probe pin 222' has a stepped surface 2221. The rear end of the retractable member 223 is connected to the stop collar 2211, and the front end of the retractable member 223 is connected to the stepped surface 2221. Since a spring is used as the retractable member 223 which is sleeved over the probe pin 222', space is saved and the overall structure of the registration target provided by the present application is further simplified. In addition, since stop collar 2211 is arranged in the housing 221 and the probe pin 222' is defined with a stepped surface 2221, the retractable member 223 can be arranged between the stop collar 2211 and the stepped surface 2221, which facilitates the installation of the retractable member 223.

In summary, the registration target provided by the present application is capable of collecting data of multiple points/point cloud data on the surface of the cartilage and/or the surface of the bone to be registered at one time or selectively, thus greatly reducing the time consuming in the registration of the bone to be registered. There is no need to manually select sampling points multiple times, which makes it more convenient in operation and effectively reduces errors in registration.

Figure 17:
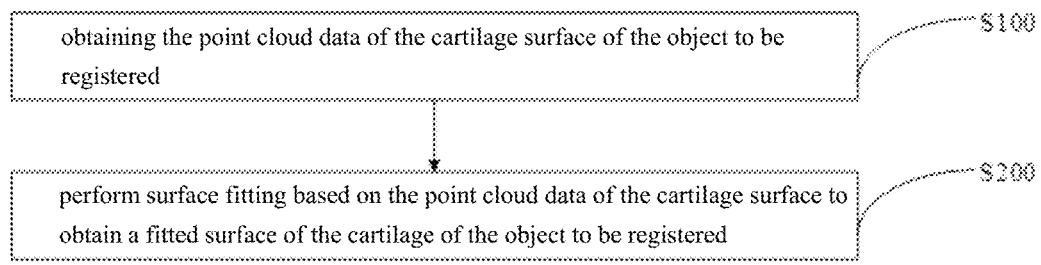
FIG. 17 is a flowchart of a registration method according to an embodiment of the present application.

The present application also provides a registration method. Please refer to FIG. 17, which schematically illustrates a flowchart of a registration method in an embodiment of the present application. As shown in FIG. 17, the registration method includes the following steps:

Step S100: obtaining the point cloud data of the cartilage surface of the object to be registered.

In step S100, the point cloud data of the cartilage surface is obtained from a collection of data of a plurality of point of the cartilage surface of the object to be registered by using the registration target described above by means of wired or wireless communication, for example.

Preferably, in this step, the point cloud data of the cartilage surface of the object to be registered can be collected through the registration target provided by the first embodiment or the third embodiment of the present application.

Step S200: perform surface fitting based on the point cloud data of the cartilage surface to obtain a fitted surface of the cartilage of the object to be registered.

Therefore, according to the registration method provided by the present application, the information of the soft tissue covering the bone surface can be obtained through fitting surfaces by using the sample points in the point cloud data of the cartilage surface, thereby providing effective information for bone ligament balance analysis.

In some embodiments, the registration method further includes the following steps:

obtaining a first point cloud data from a surface of a bone of the object to be registered;

calculating a distance from each point of the first point cloud data to the fitted surface of the cartilage;

removing, according to a first preset threshold and a second preset threshold, points with a distance greater than the first preset threshold or less than the second preset threshold from the first point cloud data of the surface of the bone to obtain a second point cloud data of the surface of the bone, where the first preset threshold is greater than the second preset threshold;

performing a spatial registration with the second point cloud data and a three-dimensional model, which is obtained in advance, of the bone of the object to be registered to obtain a mapping relationship between a model space and a real space.

The first point cloud data of the bone surface is obtained from a collection of data of a plurality of point of the bone surface of the object to be registered by using the registration target described above by means of wired or wireless communication, for example. Specifically, the point cloud data of the bone surface of the object to be registered can be collected by the registration target provided by the first embodiment of the present application to obtain the first point cloud data. In some embodiments, the point cloud data of the cartilage surface and the bone surface of the object to be registered can be collected simultaneously by the registration target provided by the second embodiment or the fourth embodiment of the present application so as to obtain the point cloud data of the cartilage surface and bone surface of the object to be registered simultaneously.

Therefore, the registration method provided by the present application can effectively eliminate the invalid points, which makes the collected points in the second point cloud data of the bone surface more accurate, and can effectively improve the registration rate. In addition, the registration method provided by the present application adopts surface registrations, which further improves the registration rate.

In some embodiments, each point of the first point cloud data of the bone surface is traversed/ergodic to calculate the distance from each point of the first point cloud data of the bone surface to the fitted surface of the cartilage.

Since the thickness of the cartilage is generally 2 mm, in the present application, the first preset threshold is preferably 2.5 mm, and the second preset threshold is preferably 0.5 mm, so that points with a distance greater than 2.5 mm or less than the 0.5 mm from the fitted surface of the cartilage are removed from the first point cloud data of the surface of the bone to obtain the second point cloud data of the surface of the bone. Therefore, after this step, inaccurate sampling points can be removed, so that the sampling points finally used for registration are more accurate, so that the registration accuracy can be effectively improved. It should be noted that the first preset threshold and the second preset threshold can be set according to specific conditions, besides the 2.5 mm and 0.5 mm listed above. The first preset threshold and the second preset threshold are set to other values, which is not limited in the present application.

In some embodiments, the process of performing a spatial registration with the second point cloud data and a three-dimensional model, which is obtained in advance, of the bone of the object to be registered specifically includes: identifying key points in the two data sets, calculating feature descriptors at each of the key points, estimating the corresponding relation based on the similarity between the features and positions from the sets of the feature descriptors and their coordinate positions in the two data sets, and estimating the rotation and translation matrix from the corresponding relation to obtain the mapping relationship between the model space and the real space.

Preferably, the three-dimensional model of the bone of the object to be registered can be obtained by segmenting and three-dimensional reconstruction of the medical image of the object to be registered. Specifically, the medical image of the object to be registered can be segmented by any one of threshold method, region growth method, edge detection method, fuzzy segmentation-based method, active contour model extraction method, or any combination thereof.

Figure 18:
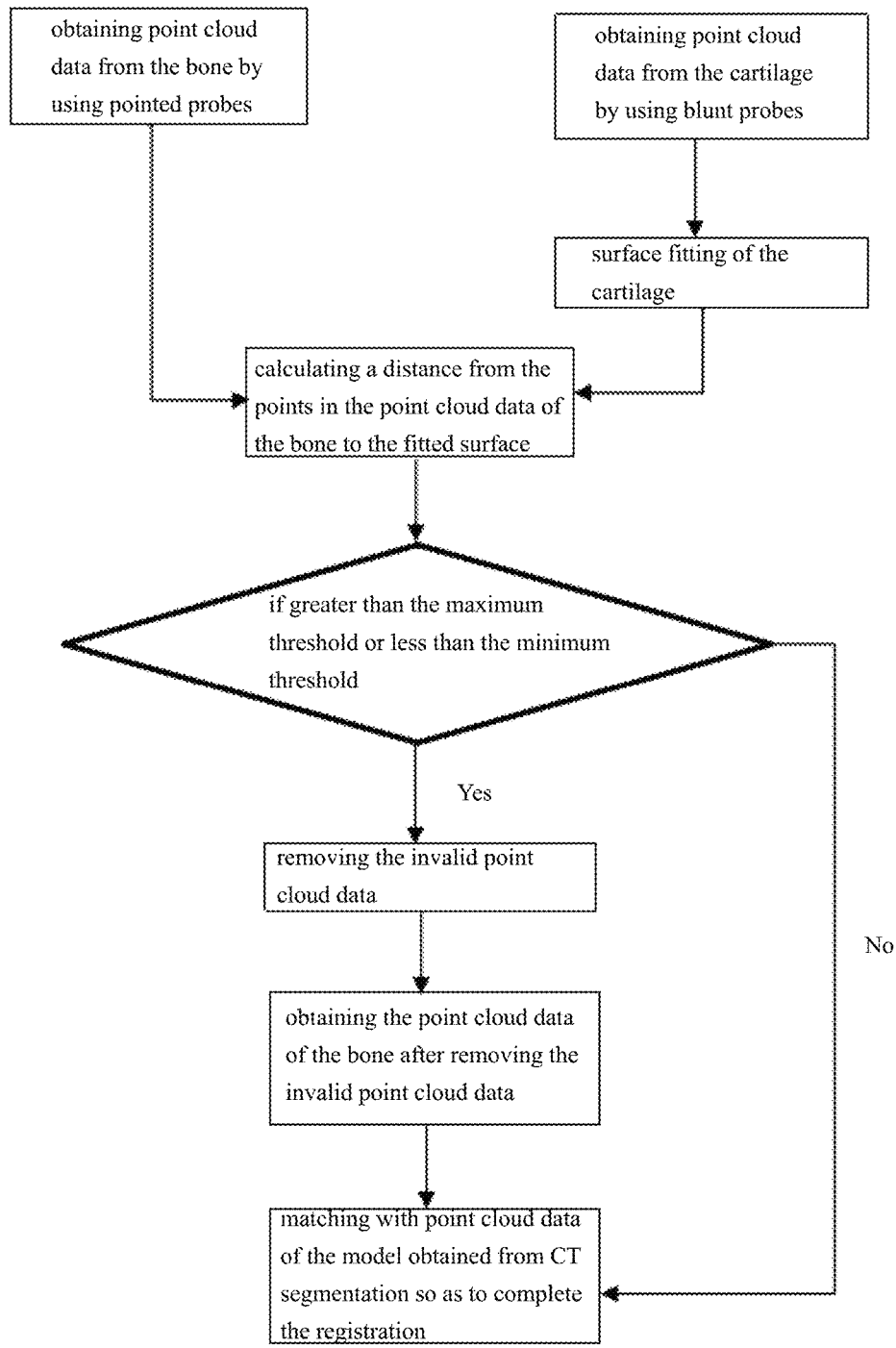
FIG. 18 is a flowchart showing specific details of a registration method according to an embodiment of the present application.

More specifically, as shown in FIG. 18 which is a flowchart of a registration method according to a specific example of the present application, the registration method includes the acquisition of the point cloud data, removal of invalid point sets, and matching process, where the matching process includes a surface matching process performed to the point cloud segmented from the CT. When a blunt probe array is used to obtain the data of the cartilage surface, data of multiple points can be collected and obtained at one time. Because of the shape of the bone, the retractable mechanism (such as the spring described above) of the blunt probe array will contract and the set of the amount of the contraction is $\Delta X=\{\Delta x\_i, i=1,2, \ldots n\}$ which represents the contraction amount of the retractable mechanism of each blunt probe in the blunt probe array, which can be converted into the displacement of the blunt probe by an information sensor. For example, in some embodiments, the information sensor is a pressure sensor. The pressure sensor is configured to obtain pressure value, and the pressure value is converted to the displacement of the blunt probe. In other embodiments, the information sensor is a distance sensor, such as an LVDT displacement sensor or a potentiometric sensor. In this case, the conversion relationship between the coordinate system of the registration target and the blunt probes is $U'=\{u\_i', i=1,2, \ldots n\}$, where $u\_i'=u\_i-\Delta x\_i$, the data of the cartilage surface obtained by the blunt probe array is $P'=\{p\_i', i=1,2, \ldots n\}$, where $p\_i'=O \cdot u\_i'$. Because of the same principle, when a pointed probe array is used to obtain the data of the bone surface, the retractable mechanism of the pointed probe array will contract because of the shape of the bone. Assuming that the set of the amount of the contraction is $\Delta Y=\{\Delta y\_i, i=1,2, \ldots n\}$, the conversion relationship between the coordinate system of the registration target and the pointed probes is $T'=\{t\_i', i=1,2, \ldots n\}$, where $t\_i'=t\_i-\Delta y\_i$, the data of the bone surface obtained by the pointed probe array is $Q'=\{q\_i', i=1,2, \ldots n\}$, where $q\_i'=O \cdot t\_i'$. In addition, the set of the points obtained by the blunt probe array needs to be fitted to a fitted surface, which is the cartilage surface information. Similarly, calculating the set of point cloud data obtained by the pointed probe array, traversing the distance from each point in the point cloud data set to the fitted surface of the cartilage, and judging according to the preset threshold judgment conditions. Generally, the thickness of the cartilage is 2 mm, the maximum threshold judgment condition can be set to 2.5 mm, and the minimum threshold judgment condition can be set to 0.5 mm. Then, it can be determined that the set of the points with a distance greater than the preset maximum threshold value or less than the preset minimum threshold value is the invalid point set. The points in the data obtained from the bone surface after excluding the invalid points and the points in the virtual model data of the bone obtained through CT segmentation in advance are used as key points to calculate the feature descriptions of key points, and then the corresponding relationship is calculated through matching the feature points. The rotation and translation matrix is estimated from the corresponding relationship between the feature points to realize the entire registration process.

In summary, according to the registration method provided by the present application, the information about the soft tissue covering the surface of bone can be obtained, thereby providing effective information for bone ligament balance analysis. Further, according to the registration method provided by the present application, invalid points can be effectively removed, so that the points collected in the second point cloud data of the bone surface are more accurate, and thus the registration rate will be effectively improved. In addition, the registration rate is further improved by adopting the surface registration.

Figure 19:
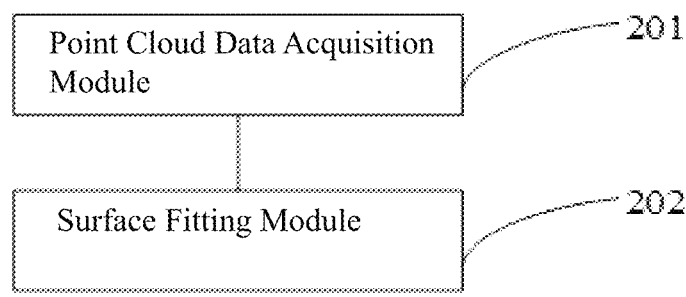
FIG. 19 is a schematic block diagram of a registration apparatus according to an embodiment of the present application.

Corresponding to the above registration method, the present application also provides a registration system comprising the registration device/target described above. Please refer to FIG. 19, which schematically illustrates a block diagram of a registration system according to an embodiment of the present application, as shown in FIG. 19, the registration system further includes:

a first point cloud data acquisition module 201 configured to obtain/receive point cloud data of a cartilage surface of an object to be registered from the collection device; and a surface fitting module 202 configured for surface fitting according to the point cloud data of the cartilage surface to obtain a cartilage surface of the object to be registered.

The point cloud data of the cartilage surface is obtained through collecting data of multiple point of the cartilage surface of the object to be registered by using the registration target described above. In some embodiments, the point cloud data of the cartilage surface of the object to be registered can be collected by the registration target provided in the first embodiment or the third embodiment of the present application.

Therefore, information about the soft tissue covering the bone surface can be obtained by the registration system provided by the present application, and effective information will be provided for bone ligament balance analysis.

Preferably, the registration device further includes:

a second point cloud data acquisition module configured to receive the first point cloud data collected by the collection device from the bone surface of the object to be registered;

a distance calculation module configured to calculate a distance from each point of the first point cloud data to the fitted surface of the cartilage;

a selecting module, configured to remove, according to a first preset threshold and a second preset threshold, points with a distance greater than the first preset threshold or less than the second preset threshold from the first point cloud data from the surface of the bone to obtain a second point cloud data of the surface of the bone, where the first preset threshold is greater than the second preset threshold; and a registration module, configured to perform a spatial registration with the second point cloud data and a three-dimensional model, which is obtained in advance, of the bone of the object to be registered to obtain a mapping relationship between a model space and a real space.

The first point cloud data of the bone surface is obtained from a collection of data of a plurality of point of the bone surface of the object to be registered by using the registration target described above. Specifically, the point cloud data of the bone surface of the object to be registered can be collected by the registration target provided by the first embodiment of the present application to obtain the first point cloud data. In some embodiments, the point cloud data of the cartilage surface and the bone surface of the object to be registered can be collected simultaneously by the registration target provided by the second embodiment or the fourth embodiment of the present application so as to obtain the point cloud data of the cartilage surface and bone surface of the object to be registered simultaneously.

Therefore, the registration method provided by the present application can effectively eliminate the invalid points, which makes the collected points in the second point cloud data of the bone surface more accurate, and can effectively improve the registration rate. In addition, the registration method provided by the present application adopts surface registrations, which further improves the registration rate.

In some embodiments, the three-dimensional model of the bone of the object to be registered can be obtained by segmenting and three-dimensional reconstruction of the medical image of the object to be registered. Specifically, the medical image of the object to be registered can be segmented by any one of threshold method, region growth method, edge detection method, fuzzy segmentation-based method, active contour model extraction method, or any combination thereof.

In summary, according to the registration system provided by the present application, the information about the soft tissue covering the surface of bone can be obtained, thereby providing effective information for bone ligament balance analysis. Further, according to the registration system provided by the present application, invalid points can be effectively removed, so that the points collected in the second point cloud data of the bone surface are more accurate, and thus the registration rate will be effectively improved. In addition, the registration rate is further improved by adopting the surface registration.

Figure 20:
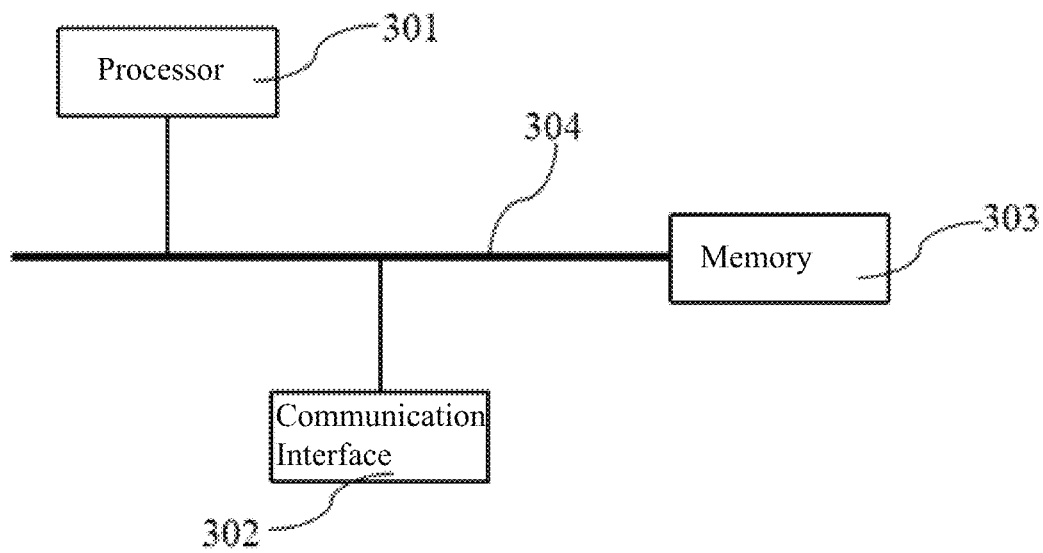
FIG. 20 is a schematic block diagram of an electronic device according to an embodiment of the present application.

The present application further provides an electronic device. Please refer to FIG. 20, which schematically illustrates a block diagram of an electronic device according to an embodiment of the present application. As shown in FIG. 20, the electronic device includes a processor 301 and a memory 303. A computer program is stored in the memory 303. When the computer program is executed by the processor 301, the registration method described above is implemented. The electronic device provided by the present application can effectively remove invalid points, so that the points collected in the second point cloud data of the bone surface are more accurate, and thus the registration rate will be effectively improved. In addition, the registration rate is further improved by adopting the surface registration.

As shown in FIG. 20, the electronic device further includes a communication interface 302 and a communication bus 304. The processor 301, the communication interface 302, and the memory 303 are configured to communicate with each other through the communication bus 304. The communication bus 304 is a Peripheral Component Interconnect (PCI) bus or an Extended Industry Standard Architecture (EISA) bus. The communication bus 304 can be divided into an address bus, a data bus, a control bus, and the like. For ease of representation, the communication bus 304 is represented by a thick line shown in the figure, but it does not mean that there is only one bus or one type of bus. The communication interface 302 is used for communication between the electronic device and other devices, and is for example a Bluetooth interface for wireless transmission or other connection interfaces for wired transmission.

The processor 301 according to the present application is selected from Central Processing Units (CPUs), or other general-purpose processors, Digital Signal Processors (DSPs), and Application Specific Integrated Circuits (ASIC), ready-made Field-Programmable Gate Array (FPGA) or other programmable logic devices, discrete gate or transistor logic devices, discrete hardware components, etc. The general-purpose processor is selected from microprocessors or other conventional processors. The processor 301 is a control center of the electronic device, and is connected to other parts of the entire electronic devices through interfaces and wires/cables.

The memory 303 is configured to store the computer program. The processor 301 is configured to execute the computer program stored in the memory 303 and call data stored in the memory 303, so that various function of the electronic device are achieved.

The memory 303 includes non-volatile and/or volatile memory. Non-volatile memory includes read-only memory (ROM), programmable ROM (PROM), electrically programmable ROM (EPROM), electrically erasable programmable ROM (EEPROM), or flash memory. Volatile memory includes random access memory (RAM) or external cache memory. RAM is available in various forms, such as Static RAM (SRAM), Dynamic RAM (DRAM), Synchronous DRAM (SDRAM), Double Data Rate SDRAM (DDRSDRAM), Enhanced SDRAM (ESDRAM), Sync Link DRAM (SLDRAM), Rambus Dynamic RAM (RDRAM), Direct Rambus RAM (DRDRAM), and Rambus DRAM (RDRAM). The communication interface receives data, for example, the point cloud data of a cartilage surface and/or the first point cloud data of the bone surface of the object to be registered, and transmitting the received data is transmitted to the processor 301 (which is, for example, a processor prearranged on a target, a robot arm processor or a processor in a general-purpose computer, which is not limited) for processing. The processor is configured to:

performing surface fitting according to the point cloud data of the cartilage surface to obtain a fitted surface of the cartilage;

calculating the distance from each point of the first point cloud data of bone surface to the fitted surface of the cartilage;

removing, according to a first preset threshold and a second preset threshold, points with a distance greater than the first preset threshold or less than the second preset threshold from the first point cloud data of the surface of the bone to obtain a second point cloud data of the surface of the bone, where the first preset threshold is greater than the second preset threshold; and performing a spatial registration with the second point cloud data and a three-dimensional model, which is obtained in advance, of the bone of the object to be registered to obtain a mapping relationship between a model space and a real space.

The present application also provides a readable storage medium. A computer program is stored in the readable storage medium. When the computer program is executed by a processor, the registration method described above is implemented. According to the readable storage medium provided by the present application, invalid points can be effectively removed, so that the points collected in the second point cloud data of the bone surface are more accurate, and thus the registration rate will be effectively improved. In addition, the registration rate is further improved by adopting the surface registration. In some embodiments, the computer program in the storage medium is processed/executed by a processor prearranged on the registration target. In other embodiments, the computer program is processed/executed by a robot arm processor or a processor in a computer. The present application does not specifically limit the device that executes the computer program.

The readable storage medium according to the embodiment of the present application adopts one of or any combination of a plurality of computer-readable media. The readable medium is a computer-readable signal medium or a computer-readable storage medium. The computer-readable storage medium is, for example, but not limited to, an electronic, magnetic, optical, electromagnetic, infrared, or semiconductor system, apparatus, or device, or any combination thereof. More specific examples (non-exhaustive list) of computer-readable storage media include: electrical connections with one or more wires, portable computer hard disks, hard disks, random access memory (RAM), read-only memory (ROM), erasable programmable read-only memory (EPROM or flash memory), optical fiber, portable compact disk read-only memory (CD-ROM), optical storage device, magnetic storage device, or any suitable combination of the foregoing. As used herein, a computer-readable storage medium is any tangible medium that contains or stores a program that can be used by one or more of an instruction execution system, apparatus, or device.

The computer-readable signal medium includes a data signal in baseband or transmitted as part of a carrier wave, which carries a computer-readable program code. Such transmitted data signal can be in many forms, including but not limited to electromagnetic signals, optical signals, or any suitable combination of the foregoing. The computer-readable signal medium is any computer-readable medium other than a computer-readable storage medium, and the computer-readable medium is configured to send, spread, or transmit a program for use by one or more of an instruction execution system, apparatus, or device.

In the embodiments described above, the point cloud data of the bone surface and the cartilage surface is obtained by using pointed probes and blunt probes so that the registration of the bone can be performed. In specific implementation, the pointed probes or blunt probes according to the present application are selectively used to obtain the information of the bone surface for providing corresponding auxiliary information to doctors.

In summary, compared with the prior art, the registration device, registration method and registration system according to the present application have the following advantages:

(1) The registration device provided by the present application includes a fixing member and a collection device connected to the fixing member, and the collecting device is configured to simultaneously collect multiple point data from an object to be registered. As a result, it is possible, by using the registration device according to the present application, to selectively or simultaneously collect data of multiple points from the cartilage surface and/or the bone surface of the object to be registered, which greatly reduces the registration time of the object to be registered. Moreover, it is also possible, by using the registration device according to the present application, to selectively or simultaneously collect point cloud data of from the cartilage surface and/or the bone surface of the object to be registered, there is no need to manually select the points to be collected, which allows a simpler operation and thus less registration error.

(2) The registration method according to the present application includes: obtaining simultaneously, by a registration device, multiple point data from a surface of a cartilage of an object to be registered; and performing surface fitting based on the multiple point data to obtain a fitted surface of the cartilage of the object to be registered. As a result, the information of the soft tissue covering the bone surface can be obtained so that useful information is available in bone ligament balance analysis.

It should be noted that the computer program code for performing the method of the present application can be written in one or more programming languages or a combination thereof. The programming languages include object-oriented programming languages such as Java, Smalltalk, C++, and also include conventional procedural programming languages, such as "C" or similar programming languages. The program code is executed entirely in the user's computer, partly in the user's computer, as an independent software package, partly in the user's computer and partly in a remote computer, or entirely in a remote computer or server. In the case of a remote computer, the remote computer can be connected to the user's computer through any kind of network, including a local area network (LAN) or a wide area network (WAN), or it can be connected to an external computer (for example through an Internet connection provided by an Internet service provider).

It should be noted that the devices and methods disclosed in the embodiments herein can also be implemented in other ways. The device embodiments described above are merely schematic. For example, the flowcharts and block diagrams in the accompanying drawings show the architecture, functions, and operations of devices, methods, and computer program products to be implemented according to various embodiments herein. In this regard, each block in the flowchart or block diagram represents a module, program, or portion of code, which contains one or more of the Executing instructions, the module, program segment or part of the code contains one or more executable instructions for implementing specified logical functions. It should also be noted that in some alternative implementations, the functions marked in the blocks also occur in a different order than those marked in the drawings. For example, two consecutive blocks are actually executed substantially in parallel, and they are sometimes executed in the reverse order, depending on the functions involved. It should also be noted that each block in the block diagrams and/or flowcharts, and combinations of blocks in the block diagrams and/or flowcharts, can be implemented in dedicated hardware-based systems to perform specified functions or actions, or it can be implemented with a combination of dedicated hardware and computer instructions.

In addition, the functional modules in the various embodiments herein are integrated together to form an independent part, or each module is provided separately, or two or more modules are integrated to form an independent part.

The above description is only a description of the preferred embodiments of the present application, and does not limit the scope of the present application. Any changes and modifications made by those of ordinary skill in the art according to the above disclosure shall fall into the protection scope of the claims. Obviously, those skilled in the art can make various modifications and variations to the application without departing from the spirit and scope of the application. In this way, if these modifications and variations of the present application fall within the scope of the claims of the present application and their equivalent technologies, the present application also intends to include these modifications and variations.

What is claimed is:

1. A registration device, comprising:
a fixing member; and
a collection device connected to the fixing member, wherein the collection device is configured to simultaneously collect multiple point data from an object to be registered;
wherein the collection device comprises:
a first collection device configured to collect a first group of point data from the object to be registered; and
a second collection device configured to collect a second group of point data from the object to be registered;
wherein the first collection device comprises a plurality of pointed probes, and the second collection device comprises a plurality of blunt probes;
wherein each of the pointed probes and/or the blunt probes comprises:
a hollow housing; and
a probe pin which is at least partially disposed in the housing and is axially moveable;
wherein the housing is connected to the fixing member, and two ends of the probe pin protrude out of the housing;
wherein a retractable member is provided in the housing;
wherein the retractable member is a spring, the retractable member is sleeved over the probe pin, an end of the housing which is close to the fixing member is provided with a stop collar, the probe pin has a stepped surface, a rear end of the retractable member is connected to the stop collar, and a front end of the retractable member is connected to the stepped surface.

2. The registration device according to claim 1, wherein the plurality of pointed probes are arranged in an array; and/or
the plurality of blunt probes are arranged in an array.

3. The registration device according to claim 1, wherein a sensor configured to measure a displacement and/or a deformation of the collection device is mounted on the collection device.

4. A registration device, comprising:
a fixing member; and
a collection device connected to the fixing member, wherein the collection device is configured to simultaneously collect multiple point data from an object to be registered;
wherein the collection device comprises at least one of:
a first collection device configured to collect a first group of point data from the object to be registered; and
a second collection device configured to collect a second group of point data from the object to be registered;
wherein the first collection device comprises a plurality of pointed probes, and the second collection device comprises a plurality of blunt probes;
wherein at least one of the pointed probes is at least partially located within one of the blunt probes and is axially movable;
wherein each of the blunt probes comprises:
a hollow housing connected to the fixing member; and
a blunt probe pin that is at least partially disposed in the housing and is axially moveable;
wherein each of the pointed probes comprises a pointed probe pin, and at least a part of the pointed probe is located in the blunt probe and is moveable axially back and forth;
wherein a first retractable member is provided in the housing, and a second retractable member is provided inside an end of the blunt probe pin that is far away from the fixing member, wherein a rear end of the first retractable member is connected to the housing, and a front end of the first retractable member is connected to the blunt probe pin; and wherein a rear end of the second retractable member is connected to the blunt probe pin, and a front end of the second retractable member is connected to the pointed probe pin.

5. The registration device according to claim 4, wherein the first retractable member and the second retractable member are both springs, the first retractable member is sleeved over the blunt probe pin, an end of the housing which is close to the fixing member is provided with a stop collar, the blunt probe pin has a stepped surface, the rear end of the first retractable member is connected to the stop collar, and the front end of the first retractable member is connected to the stepped surface; a stopper is provided inside an end of the blunt probe pin that is far away from the fixing member, the pointed probe pin comprises a horizontal portion and a vertical portion connected to the horizontal portion, the vertical portion has a pointed end that is far away from the fixing member, the rear end of the second retractable member is connected to the stopper, and the front end of the second retractable member is connected to the horizontal portion.

6. The registration device according to claim 4, wherein a sensor configured to measure a displacement and/or a deformation of the collection device is mounted on the collection device.

7. A registration device, comprising:
a fixing member; and
a collection device connected to the fixing member, wherein the collection device is configured to simultaneously collect multiple point data from an object to be registered;
wherein the collection device comprises at least one of:
a first collection device configured to collect a first group of point data from the object to be registered; and
a second collection device configured to collect a second group of point data from the object to be registered;
wherein the first collection device comprises a plurality of pointed probes, and the second collection device comprises a plurality of blunt probes;
wherein the second collection device comprises a deformation member configured to deform correspondingly to a surface to be registered after being abutted against the surface be registered;
wherein a plurality of through holes are defined in the deformation member, and each of the through holes receives a pointed probe which is axially movable;
wherein the pointed probe comprises a housing and a probe pin disposed in the housing, the probe pin is moveable back and forth along an axial direction of the housing, a rear end of the probe pin protrudes out of a rear end of the housing, a front end of the probe pin protrudes out of a front end of the housing and is received in a corresponding one of the through holes.

8. The registration device according to claim 7, wherein a retractable member is provided in the housing, a rear end of the retractable member is connected to the housing, and a front end of the retractable member is connected to the probe pin.

9. The registration device according to claim 8, wherein the retractable member is a spring, the retractable member is sleeved over the probe pin, and an end of the housing which is close to the fixing member is provided with a stop collar, the probe pin has a stepped surface, the rear end of the retractable member is connected to the stop collar, and the front end of the retractable member is connected to the stepped surface.

10. The registration device according to claim 7, wherein a sensor configured to measure a displacement and/or a deformation of the collection device is mounted on the collection device.

* * * * *